United States Patent [19]

Koller

[11] Patent Number: 4,838,790
[45] Date of Patent: Jun. 13, 1989

[54] DENTAL SLEEVE AND ITS USE

[76] Inventor: Werner Koller, Unterdorfstrasse 22,, Lausen, Switzerland, CH-4415

[21] Appl. No.: 68,187

[22] Filed: Jun. 30, 1987

[30] Foreign Application Priority Data

Jul. 7, 1986 [CH] Switzerland .................... 2739/86

[51] Int. Cl.⁴ .......................... A61C 5/08; A61C 5/10
[52] U.S. Cl. .................... 433/219; 433/218; 433/222.1; 433/223
[58] Field of Search ............ 433/218, 219, 222.1, 433/223; 219/118

[56] References Cited

U.S. PATENT DOCUMENTS

| 3,067,320 | 12/1962 | Muir | 219/118 |
| 3,934,348 | 1/1976 | Janjic | 433/222.1 |
| 4,186,172 | 1/1980 | Scholz | 422/180 |
| 4,459,112 | 7/1984 | Shoher et al. | 433/222 |
| 4,492,579 | 1/1985 | Shoher et al. | 433/222 |
| 4,698,021 | 10/1987 | Shoher et al. | 433/222.1 |

FOREIGN PATENT DOCUMENTS

| 104320 | 4/1984 | European Pat. Off. . |
| 188249 | 7/1986 | European Pat. Off. . |
| 3511487 | 8/1986 | Fed. Rep. of Germany . |
| 3523000 | 1/1987 | Fed. Rep. of Germany . |

OTHER PUBLICATIONS

*Theory and Practice of Crown and Bridge Prosthesis*, by Stanley D. Tylman, c. 1940, by C. V. Mosby Co., St. Louis, pp. 474–481.

Primary Examiner—Martin P. Schwadron
Assistant Examiner—Allen J. Flanigan
Attorney, Agent, or Firm—Wenderoth, Lind & Ponack

[57] ABSTRACT

The dental sleeve has a cylindrical or a cylindrical and conical shape having a height and circumference corresponding to that of the tooth stump or model to be enclosed. In terms of material, it is a composite foil which includes at least two layers and in which the inner layer, and optionally also the outer layer, consists of fine gold or a gold alloy, while the other layer or layers consist of platinum, palladium, silver, indium or iridium or of alloys of such metals or of alloys of such metals and gold. The cylindrical shape is produced by spot-welding the inner gold layer on the two narrow sides of the foil with a special welding technique. The dental sleeve is used as a carrier for a composite ceramic crown.

4 Claims, 4 Drawing Sheets

DENTAL SLEEVE AND ITS USE

BACKGROUND OF THE INVENTION

Various types of dental caps are known as a carrier or base on which porcelain veneer is applied, and therefore being a very important component of the finished dental crown. The crown retainer has predominantly been modelled in wax and cast in a fusing alloy.

In a new process according to European Patent Specification No. 104,320, round discs (FIG. 1) are cut out from a metal foil, prefabricated as star-shaped umbrellas (FIG. 2) and subsequently adapted manually to the tooth stump by means of special tools.

Furthermore, German Patent Specification No. 3,511,847 discloses a conical stove-pipe made of metal foil, in which several folded-out portions having a trapezoidal cross section are arranged over the periphery thereof; the stove-pipe, after being adapted to the tooth stump or model, has a three-layer outer surface at least in an edge region thereof, that is to say in the subsequent cervical region.

However, manual shaping is time-consuming, is subject to considerable fluctuations attributable to the individual performance thereof by the dental technician, and causes uneven folding leading to a large loss of mechanical strength. Random or angular folding results in stresses in the ceramic mass. In general, the production tolerance of the materials associated with manual shaping is very high because such must be manipulated by different dental technicians; material tests have shown that the laborious folding by hand of the umbrella or stove-pipe results in uneven inner faces which fail to form plane diffusion surfaces. The subsequent diffusion of the layer of pure gold by fusion to form a compact closed cap is often incomplete. The results are edge deformation, inaccuracy of fit and ceramic chipping.

According to German Offenlegungsschift No. 3,523,000, a metal foil which lays itself automatically against the tooth stump as soon as a force K is exerted on it from outside is used (FIG. 3). Under the effect of the above-mentioned force, the metal foil lays itself onto the surface of the tooth stump 1, linear vertical folds 2 being defined at equal distances from one another (FIG. 4). The number of loop-shaped folds and the interspaces are calculated so that, for example, a double folding strip 3 (FIG. 5) or a strip-like vertical strut 4 (FIG. 6) is obtained.

Accordingly, the tooth-crown retainer thereby formed consists of one or more metal layers, depending on the folding pattern and the arrangement in the pattern. Like the above-mentioned caps according to EP No. 104,320 and DE No. 3,511,847, at its lower edge or at the gingival margin, that is to say precisely where it is to provide a tight seal, it has a thickness which is irregular because of the folds, and this has a disruptive effect especially in the cervical and labial region and can lead to deformations in the subsequent dental crown and consequently to instability or only partial accuracy of the fit.

SUMMARY OF THE INVENTION

An object of the present invention is to provide a new dental sleeve that does not have the disadvantages described above, to be used as a carrier for the porcelain veneer of a composite ceramic crown.

BRIEF DESCRIPTION OF THE DRAWINGS

In the following the preferred embodiments of the invention will be described with reference to the accompanying drawings in which.

DETAILED DESCRIPTION OF THE PREFERRED EMBODIMENTS

The new dental sleeve according to the present invention can be used directly on tooth stumps having conventional anatomical shapes (FIGS. 7, 8a, 8b, 9a and 9b).

Figure 11:
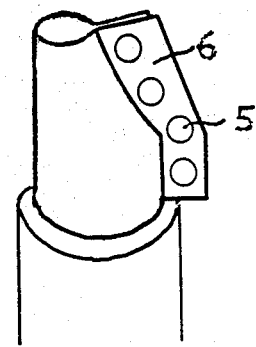
FIG. 11 shows a second embodiment of the invention as applied to the tooth stump of FIGS. 8a/8b.
Figure 12:
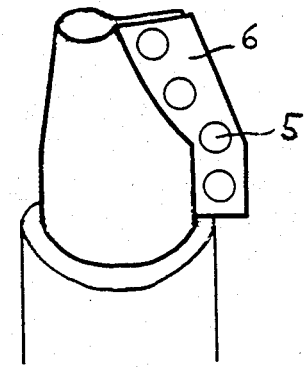
FIG. 12 shows a third embodiment of the invention as applied to the tooth stump of FIGS. 9a/9b.

The sleeve according to the invention consists of a composite foil having a cylindrical form (FIG. 10), a cylindrical bottom and lingually shaped conical top (FIG. 11), or a lingually and laterally conical shape (FIG. 12). In terms of material, it consists of at least two layers, the inner layer, and optionally also the outer layer when three or more layers are employed, consisting of fine gold or a gold alloy, while the other layer or layers consist of platinum, palladium, silver, indium or iridium or of an alloy or alloys comprising at least two of these metals or at least one of these metals and gold or of a slightly reduced fusing alloy. The above-mentioned shape of the sleeve is established by means of spot welds 5 on the inner fine-gold or gold-alloy layer on the two narrow sides of the composite foil, while the height and circumference of the sleeve are selected in conformity with those of the tooth stump or model to be enclosed.

However, until recently it has been virtually impossible to bond gold foils or metal foils coated with gold or with gold alloy to one another by means of spot welding. When conventional welding appliances having copper electrodes were used, a hole formed at too high a voltage, whereas welding did not take place at too low a voltage. Since, in the present dental sleeve, the spot welds of the precious-metal composite foil are a constructional requirement and the welding technique for this requirement had to be developed, the present invention could not be derived from the dental caps of the patent specifications mentioned in the introduction.

The invention is further described in detail below.

The composite foil advantageously has a total thickness of approximately 0.06 mm. It is a rolled sandwich foil, of which at least one layer (depending on the manufacturing company, i.e. gold and silver parting institutions) generally consists of an alloy comprising two or more of the metals platinum, palladium, silver, indium, iridium and gold or of a slightly reduced fusing alloy. A slightly reduced fusing alloy refers to an alloy comprising at least 50% of fine gold. In most cases, however, there are more than only one such layer, resulting in a laminate; the single layers, then, may consist of metals or alloys different than those mentioned above. One or both surfaces of the above-mentioned layer or laminate are covered with a fine gold layer or a gold-alloy layer; these can also be fine-gold granular layers.

Figure 1:
FIGS. 1-6 illustrate the prior art.
Figure 2:
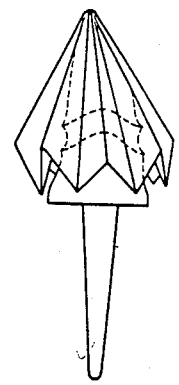
Figure 3:
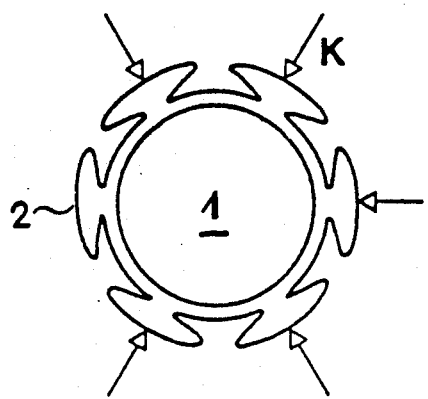
Figure 4:
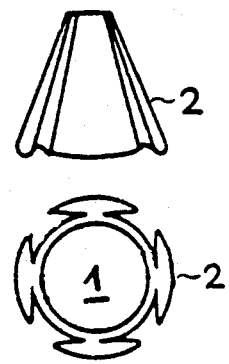
Figure 5:
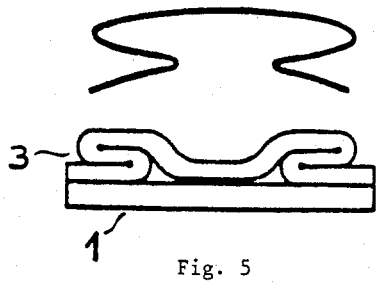
Figure 6:
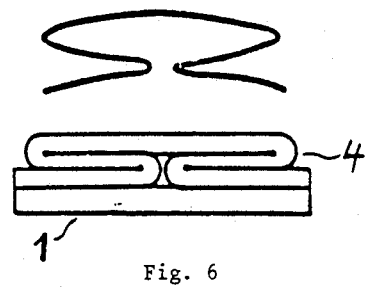
Figure 7:
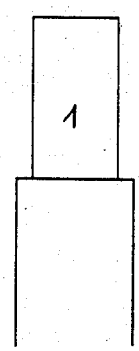
FIG. 7 illustrates a first type of a conventional tooth stump.
Figure 8A:
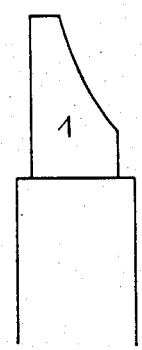
FIGS. 8a and 8b are a side view and a perspective view of a second type of a conventional tooth stump.
Figure 8B:
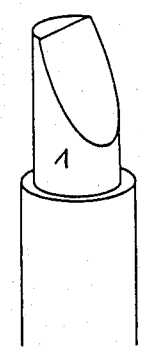
Figure 9A:
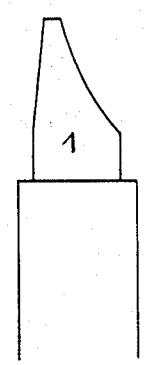
FIGS. 9a and 9b are a side and a front view of a third type of a conventional tooth stump.
Figure 9B:
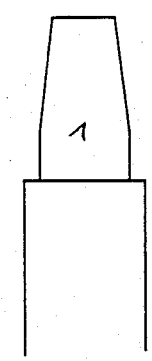
Figure 10:
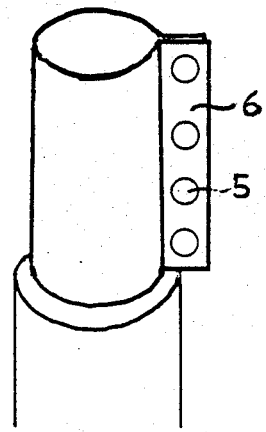
FIG. 10 shows a first embodiment of the invention as applied to the tooth stump of FIG. 7.
Figure 13:
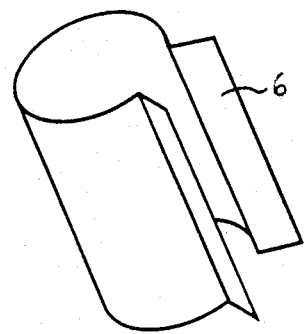
FIG. 13 is a perspective view of a sleeve before it is assembled by spot welding.

The composite foil, for instance, may have in the following composition:

1st layer: fine gold
2nd layer: alloy of Au, Pt, Pd and Ag, e.g. Au 80%, Pt 10%, Pd 5% and Ag 5%
3rd layer: alloy of Pd, Ag and Au or Pd, Ag and Ir, e.g. Pd 55%, Ag 5% and Au 35% or Pd 80%, Ag 12% and Ir 8%
4th layer: same as the 2nd layer
5th layer: fine gold To produce the dental sleeve, the foil is first cut into rectangular pieces, the width and length of which correspond to the height and circumference of the sleeve or the tooth stump or model to be enclosed, plus the weld segment 6. The cut pieces are then shaped into cylinders on specially adapted tools, the edges of the narrow sides not overlapping, but resting against one another at the outside (FIG. 13), so that the inner gold layer or gold-alloy layer on one narrow side and the same layer on the other narrow side rest on one another. The edges of the narrow sides, arranged in this way, are then joined to one another over the height of the cylinder by means of spot welding (FIG. 10).

Figure 14:
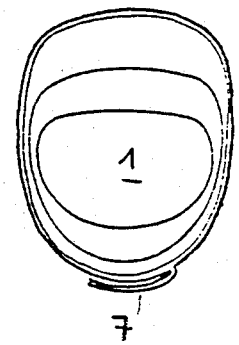
FIG. 14 is a sectional view of a sleeve mounted on the corresponding tooth stump.

The importance of the spot welding has already been stressed. It is advantageously carried out by means of spot-welding appliances designed specifically for welding these components by having wolfram (tungsten) electrodes. However, spot welding by the use of laser beams is also possible. In general, the welds are made and the welded segment 6 is disposed on the lingual side 7 of the tooth stump (FIG. 14).

To produce dental sleeves having the second shape mentioned above, that is to say cylindrical at the bottom and lingually conical at the top (FIG. 11), the spot welding is carried out in the lower part of the cylinder only, the cylinder is pressed, above the welded part, against the lingual side of the tooth stump or model so that the upper part of the cylinder acquires a conical shape, and the protruding edges are joined together in the upper unwelded part by spot welding along the incline surface defining the cone.

Figure 15:
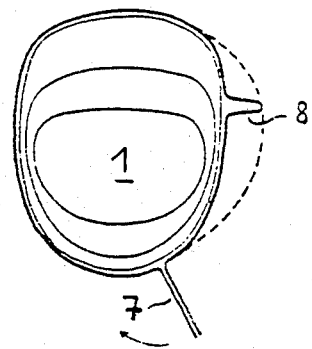
FIG. 15 is a sectional view of a further embodiment of the sleeve mounted on the tooth stump.

When dental sleeves having the third shape mentioned above, that is to say the lingually and laterally conical shape (FIG. 12), are to be produced, then, in addition to the steps mentioned above, one or two protruding folds 8 will be formed at one end or at both ends of the transverse axis by drawing in the upper part and pressing it together (FIG. 15), and the protruding fold or protruding folds will be cut off to make fusion diffusion easier in the production of the composite ceramic crown.

Thus, prefabricated dental sleeves are obtained, and have one of three above-mentioned shapes illustrated in FIGS. 10, 11 and 12, the height and circumference of which correspond to those of a particular tooth-stump size chosen and which can be fabricated in the form of models having a range of dimensions. The sleeves will fit flush around the cervical stump part (preparation limit), with an excess length in relation to the lowest cervical preparation point of 1.5 to 2.0 mm.

Each model within a range thus represents a standardized collar, the circumference of which will correspond to the cervical part of the particular tooth stump. The circumference of the cervical part can be measured by means of a dentimeter; the suitable model is then selected from the various models on the basis of the measurement obtained.

Figure 16:
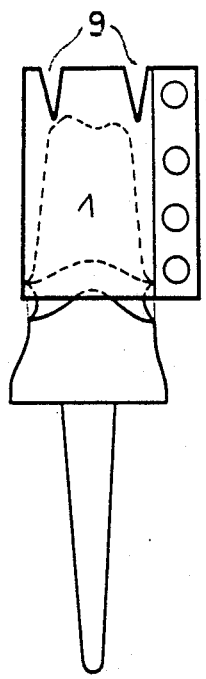
FIG. 16 is a side view of the sleeve for producing a composite ceramic crown.
Figure 17:
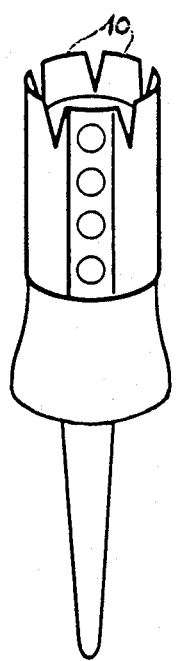
FIGS. 17 to 21 are perspective views of other embodiments according to the present invention.
Figure 18:
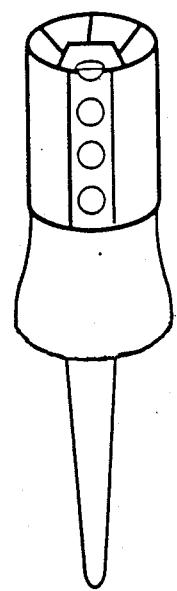
Figure 19:
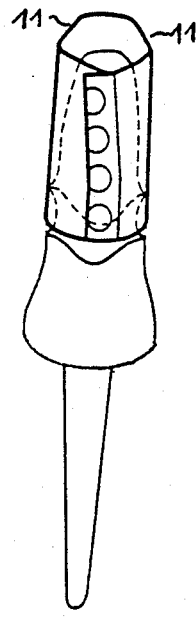
Figure 20:
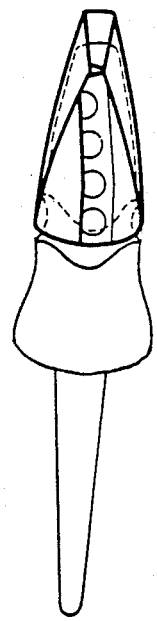
Figure 21:
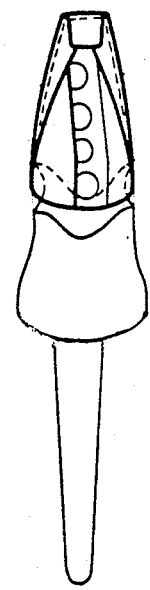
Figure 22:
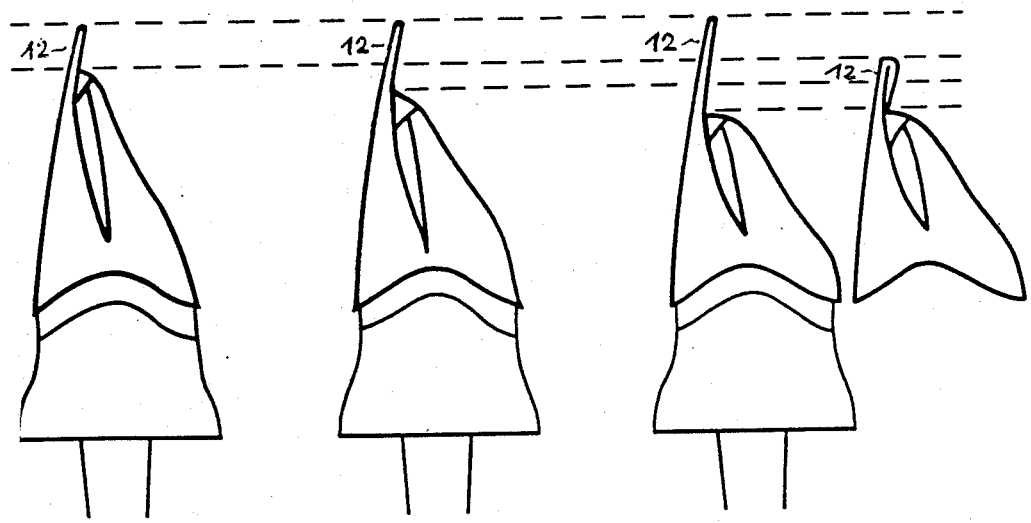
FIG. 22 shows four different successive steps in a method of using the sleeve.

According to the invention, these dental sleeves are used for producing composite ceramic crowns, by carrying out an accurate matching of the dental sleeve to the dimensions of the tooth stump and at the same time bending the upper edges of the sleeve towards each other, so that the upper orifice is closed. For this purpose, cut-outs 9 are made in the upper marginal portion of the cylinder (FIGS. 16 and 17) and the remaining protruding portions 10 are bent against the center of the sleeve (FIG. 18). In the sleeve having the conical shape, the sides 11 of the sleeve are bent towards each other in the upper part (FIGS. 19 and 20) and the remaining opening is then closed according to a known procedure (FIG. 21). If the porcelain jacket provided on the sleeve is too thick in relation to the height of the tooth stump to ensure the satisfactory static behavior of the tooth crown, the upper edges can be drawn together into an incisal fold 12 (FIG. 22). If appropriate, the mesial and distal sides of the sleeve are also drawn together to form a fold (FIG. 15) or folds. If only the inner layer of the dental sleeve consists of fine gold or a gold alloy, in addition a corresponding outer layer is applied to the sleeve, advantageously by means of an appropriate paste. The dental sleeve matched in this way is then heated to a temperature of approximately 1030° to approximately 1080° C., preferably in a gas flame 13 (FIG. 23) or in an oven, for diffusion of the fine-gold layers or gold-alloy layers by fusion. An adhesion promotoer or a binder for the porcelain veneer is then coated on the dental sleeve and fused thereon, and the ceramic mass is applied to the dental sleeve and fused to it.

Before the dental sleeve is used, a precondition exists in which the model stump is to be trimmed and a groove is to be made exactly underneath the preparation limit, followed by subsequent cylindrical filling with a special blocking-out plastic (for example, Uniblock or Zappite). Any recesses in the tooth stump will also be filled. This preparation phase is well known to the dental technician.

It is preferable to proceed particularly in accordance with the following working steps.

(a) Adapting tihe sleeve, while at the same time allowing for an excess length of 2.0 to 3.0 mm, to the incisal tip 12 of the model stump (FIG. 22).

(b) Should further adaptation be necessary in the cervical peripheral region of the sleeve, an individual bracing fold 8 (FIG. 15) can be made on the mesial or distal side of the model stump, that is to say a sleeve selected with too large a circumference can thus be matched closely to and flush with the preparation limit.

(c) Accurate excision of the cervical edge seal part by means of micro-shears to a residual part of approximately 1.0 mm below the preparation edge.

(d) By the use of a conventional hammer press (swager) with a maleable base foil of approximately 0.015 to 0.020 mm, adaptation is carried out by means of 2 to 3 moderate hammer blows.

Figure 23:
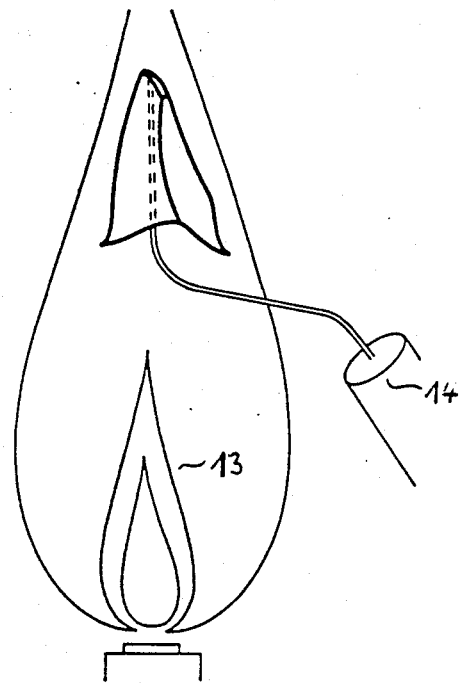
FIG. 23 shows a step of heating the sleeve for facilitating the diffusion of the gold layer.

(e) Vertical diffusion by fusion in a Bunsen burner while held with a special wire holder 14 shown FIG. 23 or in an oven.

(f) Fine adjustment according to a process already known.

(g) Acid treatment or sand-blasting with aluminium oxide having very fine granules, degreasing.

(h) Fusing on of a conventional adhesion promoter (bonder, masking gold, bonding gold), fine-film baking (wash baking), first baking, dentine baking, etc; fusing on is carried out in the same way as with a cast cap.

The advantages arising from the invention can be summarized as follows:

Extremely efficient production, in terms of time, of a precious-metal carrier sleeve for carrying subsequently formed composite ceramic crown, doing away with the conventional cast cap.

A single uniform layer in the labial and cervical region and therefore a better cervical edge seal and a cosmetically perfect appearance.

The capability of the upper incisal part of the sleeve to be pressed into an incisal fold 12 (FIG. 22) thereby, according to the porcelain and manufacturer's recommendation, ensuring a static support of the porcelain veneer when the stump is too short in relation to the height of the tooth crown.

Economical consumption of precious metal because of exactly sized precut pieces for the particular stump size.

Cut pieces, the three above-mentiond basic of which are matched to the particular stump shapes.

I claim:

1. A dental sleeve adapted to enclose a tooth stump or a model for supporting a ceramic veneer in a composite ceramic crown, said dental sleeve consisting of a composite foil, the composite foil having a weld segment and either a cylindrical portion, or a cylindrical bottom portion and a top portion that is defined by a front surface, lateral surfaces and a rear surface corresponding to the lingual surface of the crown, of said surfaces, only the rear surface or the rear surface and the lateral surfaces inclined in a radially inward direction from the cylindrical bottom portion, the composite foil comprising at least two layers including an inner layer and an outer layer, of the inner and the outer layers, at least said inner layer consisting of fine gold or a gold alloy, each of the remaining layer or layers consisting of either one of a group consisting of platinum, palladium, silver, indium, and iridium, or an alloy or alloys of at least two metals in said group, or at least one of the metals in said group and gold, or of an alloy made up of at least 50% of fine gold, and said weld segment extending over the length of the sleeve and along which spot welds are disposed at which portions of said inner layer are joined to one another.

2. A method of producing a dental sleeve consisting of a composite foil for supporting a ceramic veneer in a composite crown, the composite foil have at least two layers including an inner layer and an outer layer, of the inner and the outer layers, at least said inner layer consisting of fine gold or a gold alloy, each of the remaining layer or layers consisting of either one of a group consisting of platinum, palladium, silver, indium, and iridium, or an alloy or alloys of at least two metals in said group, or at least one of the metals in said group and gold, or of an alloy made up of at least 50% of fine gold, and said method comprising:

providing a tooth stump or model having at least a cylindrical portion;

cutting the composite foil into a rectangular piece defined by a central rectangular section and a respective weld segment extending from each of the shorter sides of said rectangular section, the width of said central rectangular section corresponding to the length of the tooth stump or model, and the length of the central rectangular section corresponding to the circumference of the cylindrical portion of the tooth stump or model;

shaping the rectangular piece of composite foil into a cylinder around the cylindrical portion of the tooth stump or model with the shorter sides of the central rectangular section abutting one another in a nonoverlapping manner and with the weld segments confronting each other and extending over the length of the tooth stump or model; and spot welding the inner layer of the composite foil at one of the weld segments to the inner layer of the composite foil at the other of the weld segments thereby securing the composite foil around the tooth stump or model with the shorter sides of the central rectangular section aligned.

3. A method as claimed in claim 2, wherein said step of providing a tooth stump or model comprises providing a tooth stump or model having a cylindrical bottom and a top portion that is defined by a front surface, lateral surfaces and a rear surface corresponding to the lingual surface of the crown, the rear surface being inclined radially inward from the cylindrical bottom, said step of spot welding is performed in two stages, the first of said two stages comprising spot welding the inner layer of the composite foil at the weld segments only adjacent the cylindrical bottom of the tooth stump or model, said step of shaping comprises shaping the rectangular piece of composite foil into a cylinder with the weld segments confronting each other adjacent the rear surface of the top portion, and further comprises pressing the composite foil against the rear surface after said first stage of spot welding is performed, the second of said two stages of spot welding comprising spot welding the inner layer of the composite foil at the weld segments adjacent the rear surface of the top portion of the tooth stump or model after the composite foil has been pressed thereagainst.

4. A method as claimed in claim 3, wherein said step of providing a tooth stump or model comprises providing a tooth stump of which the lateral surfaces of the top portion are also inclined radially inward from the cylindrical bottom, wherein said step of shaping further comprises pressing the composite foil against the lateral surfaces of the top portion of the tooth stump or model in a manner in which at least one protruding fold is formed extending transversely with respect to the central longitudinal axis of the cylindrical bottom of the tooth stump model, and further comprising cutting off each said at least one protruding fold.

* * * * *